United States Patent [19]

Takagaki et al.

[11] Patent Number: 5,225,605
[45] Date of Patent: Jul. 6, 1993

[54] PROCESS FOR PRODUCING PYRETHROLONE AND ITS INTERMEDIATE COMPOUND

[75] Inventors: Tohei Takagaki, Nishinomiya; Noritada Matsuo, Itami, both of Japan

[73] Assignee: Sumitomo Chemical Company, Limited, Osaka, Japan

[21] Appl. No.: 897,064

[22] Filed: Jun. 11, 1992

[30] Foreign Application Priority Data

Jul. 1, 1991 [JP] Japan ............................. 3-160471

[51] Int. Cl.$^5$ ............................................. C07C 45/62
[52] U.S. Cl. ............................. 568/347; 568/348
[58] Field of Search .............................. 568/347, 348

[56] References Cited

FOREIGN PATENT DOCUMENTS 3-14541 1/1991 Japan .................................. 568/341

OTHER PUBLICATIONS

Agric. Biol. Chem., 54(9), 2473-2476, 1990, Millar: "Synthesis of 9Z, 11E, 13-Tetradecatrienal, the Major Component of the Sex Pheromone of the Carob Moth, *Ectomyelois ceratoniae* (Lepidoptera: Pyralidae)".
Ratovelomanana et al., Tet. Letters, vol. 22, pp. 315-318 (1981).
Naf et al., Helv. Chim. Acta, vol. 58, pp. 1016-1036 (1975).
Boland et al., Helv. Chim. Acta., vol. 70, pp. 1025-1040 (1987).
Journal of the Chemical Society 1956, Letchworth GB, pp. 3963-3971, L. Crombie et al., "Experiments on the Synthesis of the Pyrethrins. Part XI. Synthesis of cis-Pyrethrolone and cis-Pyrethrin I: Introduction of the cis-Penta-2: 4-dienyl System by Selective Hydrogenation," pp. 3963, 3965, 3969.
Chemical Abstracts, vol. 114, 1991, Columbus, Ohio, US; abstract No. 246862v, Tkakagaki, Tohei et al., "Preparation of 4-oxo-2-methyl-3-(4-penten-2-ynyl-)-2-cyclopentenyl esters as intermediates for pyrethrins", p. 719; column 2; & JP-A-3 014 541 (Sumitomo Chemical Company, Ltd.), 23 Jan. 1991.

*Primary Examiner*—James H. Reamer
*Attorney, Agent, or Firm*—Stevens, Davis, Miller & Mosher

[57] ABSTRACT

Pyrethrolone of the formula [II],

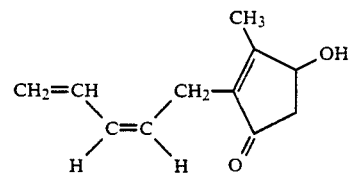

is produced by reacting a cyclopentenolone derivative of the formula [I],

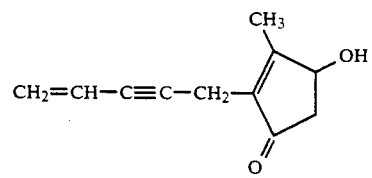

with zinc in an aqueous alcohol solvent. And the cyclopentenolone derivative of the formula [I] is produced by reacting a propargylcyclopentenolone derivative of the formula [III],

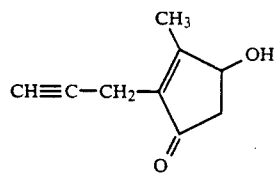

with vinyl halide in the presence of a palladium catalyst, a copper catalyst and a tertiary amine. These processes permit easy production of pyrethrolone of the formula [II] and an intermediate compound of the formula [I] for the production of the pyrethrolone.

9 Claims, No Drawings

PROCESS FOR PRODUCING PYRETHROLONE AND ITS INTERMEDIATE COMPOUND

The present invention relates to a process for producing pyrethrolone useful as an intermediate compound for the synthetic production of insecticidal natural pyrethrins, and a process for producing a cyclopentenolone derivative as an intermediate compound for the production of pyrethrolone.

A conventionally known process for producing pyrethrolone is a process described in J. Chem. Soc., 3963 (1956).

However, the process cannot be said to be satisfactory due to the low yield of a pyrethrolone of the formula [II] below produced by the hydrogenation of a cyclopentenolone derivative of the formula [I] below in the presence of a Lindlar catalyst, and due to the low purity of the produced pyrethrolone by the low selectivity to hydrogenation of the triple bond as compared with the double bonds during the hydrogenation reaction (J. Chem. Soc. (C), 1016 (1969)). Moreover, the cyclopentenolone derivative of the formula [I], an intermediate compound, is prepared only by a complicated manner.

As a result of a diligent study to overcome the above problems, the present inventors have found that a pyrethrolone of the formula [II],

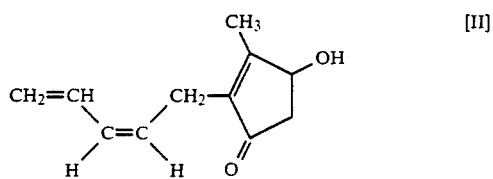

can be produced at high yields with high purity by reacting a cyclopentenolone derivative of the formula [I],

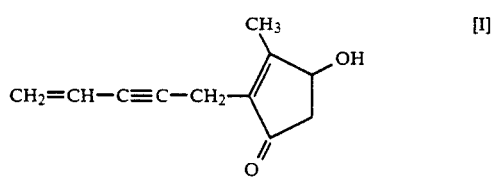

with zinc in an aqueous alcohol solvent; and that the cyclopentenolone of the formula [I], an intermediate compound for the production of the pyrethrolone of the formula [II], can be easily produced without the necessity to protect a hydroxyl group by reacting a propargylcyclopentenolone derivative of the formula [III],

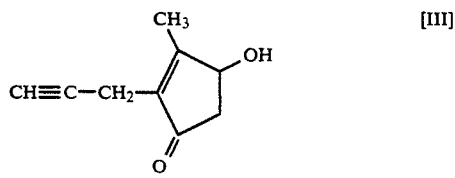

with vinyl halide in the presence of a palladium catalyst, a copper catalyst and a tertiary amine. The present invention has been completed on the basis of the above findings.

According to the present invention, there are provided a process for producing a pyrethrolone of the formula [II] which comprises the step of reacting a cyclopentenolone derivative of the formula [I] with zinc in an aqueous alcohol solvent; a process for producing a pyrethrolone of the formula [II] which comprises the steps of reacting a propargylcyclopentenolone of the formula [III] with vinyl halide in the presence of a palladium catalyst, a copper catalyst and a tertiary amine to obtain a cyclopentenolone derivative of the formula [I] and reacting the cyclopentenolone derivative with zinc in an aqueous alcohol solvent; and a process for producing a cyclopentenolone derivative of the formula [I] which comprises the step of reacting a propargylcyclopentenolone derivative of the formula [III] with vinyl halide in the presence of a palladium catalyst, a copper catalyst and a tertiary amine.

As the zinc used for the reduction reaction of the cyclopentenolone of the formula [I], powdery or granular zinc is preferred. Although a commercially available zinc may be used as it is, preferred is such a zinc that is activated by a method described in "Reagents for Organic Synthesis", Vol. 1, page 1,276 (1967) by Fieser et al. The amount used of zinc is usually within the range of from 1 to 200 equivalents, preferably within the range of from 5 to 200 equivalents per equivalent of the cyclopentenolone of the formula [I].

Specific examples of the aqueous alcohol solvent are mixtures of a $C_1$-$C_4$ alcohol such as 1-propanol and 2-propanol, and water whose volume is between 10 and 160% per 100% by volume of the alcohol. Usually used are aqueous alcohols containing about 50% by volume of water.

The reaction can be carried out at a temperature of 20° to 150° C. It is usually carried out at the reflux temperature of the solvent used. The reaction time is usually within 100 hours.

Specific examples of the vinyl halide used for the production of the cyclopentenolone derivative of the formula [I] are vinyl chloride, vinyl bromide and vinyl iodide. The amount used of the vinyl halide is usually from 1 to 20 equivalents per equivalent of the propargylcyclopentenolone of the formula [III].

Any palladium catalyst that can generate palladium having a valence of zero can be used as such. Specific examples of the palladium catalyst are palladium phosphine complexes such as tetrakis(triphenylphosphine)palladium, bis(triphenylphosphine)palladium dichloride, bis(diphenylphosphine)ethanepalladium dichloride and bis(triphenylphosphine)palladium acetate. The amount used of the palladium catalyst falls usually within the range of from 0.001 to 0.5 mole per mole of the propargylcyclopentenolone derivative of the formula [III].

As the copper catalyst, cuprous halides such as cuprous chloride, cuprous bromide and cuprous iodide are usually used. Particularly preferred is cuprous iodide. The amount used of the copper catalyst is usually within the range of from 0.001 to 0.5 mole per mole of the propargylcyclopentenolone derivative of the formula [III].

Specific examples of the tertiary amine are those having three lower alkyl (usually $C_1$-$C_4$ alkyl) groups such as triethylamine, tributylamine and diisopropylethylamine. The amount used of the amine is usually within the range of from 1 to 10 moles per mole of the propargylcyclopentenolone derivative of the formula [III].

The reaction temperature is usually in the range of from 5° to 50° C., preferably in the range of from 15° to 25° C. The reaction time is usually within 24 hours. This reaction is usually carried out in a solvent such as aromatic hydrocarbons (e.g. toluene and benzene), ethers (e.g. tetrahydrofuran and dioxane), halogen-containing solvents (e.g. chloroform and methylene chloride), dimethylformamide and acetonitrile.

In the present invention, the use of the racemic mixture or one of the optical isomers of the propargylcyclopentenolone derivative of the formula [III] can easily give the racemic mixture or one of the optical isomers of the cyclopentenolone derivative of the formula [I], respectively, which mixture or one of the optical isomers in turn is easily converted to the racemic mixture or one of the optical isomers of the pyrethrolone of the formula [II]. The use of an optically active starting material enables the production of an optically active product retaining the configuration without suffering racemization during the intermediate steps.

The propargylcyclopentenolone derivative of the formula [III] can be obtained, for example, by a method described in U.S. Pat. No. 4,356,326. The optical isomer thereof can be obtained, for example, by a method described in U.S. Pat. No. 4,385,186.

EXAMPLES

The present invention will be described further in detail hereinafter by reference to Examples. However, the present invention should not be interpreted to be limited thereto.

Preparation Example 1

Preparation of (+)-(S)-pyrethrolone

Under nitrogen atmosphere, 300 ml of a 0.1N hydrochloric acid aqueous solution was added to 300 g of a zinc powder and the mixture was stirred for 15 minutes. The hydrochloric acid aqueous solution was removed by decantation, and the residue was washed with 300 ml of distilled water twice. After 150 ml of distilled water had been added to the washed residue, a solution of 5.0 g of (+)-(S)-2-methyl-3-(pent-4-en-2-ynyl)cyclopent-2-en-4-one-1-ol in 150 ml of 1-propanol was added thereto. The resultant mixture was allowed to react at the reflux temperature for 30 hours. After cooling the reaction mixture, the reaction liquid was separated by decantation. The procedures of washing the residue with 100 ml of ethyl acetate and removing the ethyl acetate by decantation were repeated five times. The reaction liquid and the wash liquid were mixed, and the mixture was washed with dilute hydrochloric acid and then with water. The organic layer was dried over anhydrous magnesium sulfate, and the solvent was distilled off under reduced pressure. The remainder was subjected to Florisil column chromatography (elution solvent; diethyl ether:in-hexane=1:1) to obtain 4.3 g of the intended (+)-(S)-pyrethrolone.

$[\alpha]_D^{24}+16.2°$ (c=1.1, CHCl$_3$)

Value from literature $[\alpha]_D^{22}+15.6°$ (c=2.0, CHCl$_3$) [J. Agric. Food Chem. 31, 151 (1983)]

$^1$H-NMR (in CDCl$_3$, Internal standard: TMS)

δ-value (ppm) 1.85 (br. s, 1H), 2.10 (s, 3H), 2.25 (dd, 1H), 2.80 (dd, 1H), 3.05 (d, 2H), 4.70 (d, 1H), 5.10–5.50 (m, 3H), 6.00 (c, 1H), 6.75 (ddd, 1H)

Preparation Example 2

Preparation of (+)-(S)-2-methyl-3-(pent-4-en -2-ynyl)cyclopent-2-en-4-one-1-ol

10 Grams of (+)-(S)-2-methyl-3-propargylcyclopent-2-en-4-one-1-ol was dissolved in 100 ml of benzene. Thereto were added successively 3.85 g of tetrakis(triphenylphosphine)palladium, 1.27 g of cuprous iodide and 13.5 g of triethylamine. 150 Grams of vinyl bromide was promptly added to the resultant mixture. The mixture was stirred under nitrogen atmosphere at room temperature overnight. Thereafter, the mixture was poured on dilute hydrochloric acid. A benzene layer was recovered from the mixture, and the water layer was further extracted with benzene. The benzene layers were mixed, washed with saturated brine, and dried over anhydrous magnesium sulfate. The solvent was distilled off under reduced pressure. Methanol was added to the residue, and insolubles were removed by filtration. The filtrate was concentrated under reduced pressure, and the residue was subjected to silica gel column chromatography (elution solvent; hexane:ethyl acetate=3:1) to obtain 7.5 g of (+)-(S)-2-methyl-3-(pent-4-en-2-ynyl)-cyclopent-2-en-4-one-1-ol.

$[\alpha]_D^{25}+23.0°$ (c=1.0, CHCl$_3$)

$^1$H-NMR (in CHCl$_3$, Internal standard: TMS)

δ-value (ppm) 2.15–2.38 (m, 4H), 2.65–2.93 (m, 2H), 3.20 (s, 2H), 4.70 (m, 1H), 5.26–5.73 (m, 3H).

Preparation Example 3

Preparation of (RS)-pyrethrolone

Repeating the procedure of Preparation Example 1 with replacing (+)-(S)-2-methyl-3-(pent-4-en-2-ynyl)-cyclopent-2-en-4-one-1-ol by a mixture of the (RS)–isomers thereof gives 4.2 g of (RS)-pyrethrolone.

Preparation Example 4

Preparation of (RS)-2-methyl-3-(pent-4-en-2-ynyl)cyclopent-2-en-4-one-1-ol

Repeating the procedure of Preparation Example 2 with replacing (+)-(S)-2-methyl-3-propargylcyclopent-2-en-4-one-1-ol by a mixture of the (RS)-isomers thereof gave 7.3 g of (RS)-2-methyl-3-(pent-4-en-2-ynyl)-cyclopent-2-en-4-one-1-ol.

According to the processes of the present invention, pyrethrolone of the formula [II] and an intermediate of the formula [I] for the production of the pyrethrolone can be easily produced.

What is claimed is:

1. A process for producing a cyclopentenolone derivative of the formula (I)

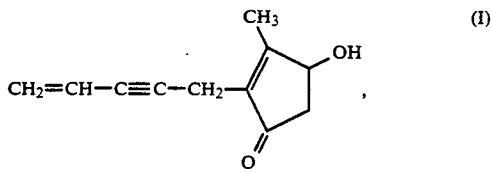

which comprises the step of reacting a propargylcyclopentenolone derivative of the formula

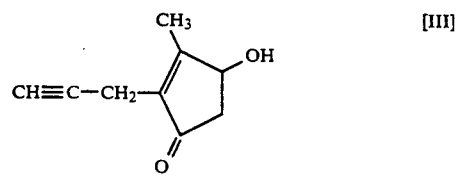

with vinyl halide in the presence of a palladium catalyst, a copper catalyst and a tertiary amine.

2. A process for producing pyrethrolone of the formula (II)

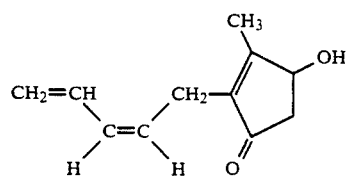

which comprises the steps of reacting a propargylcyclopentenolone derivative of the formula (III)

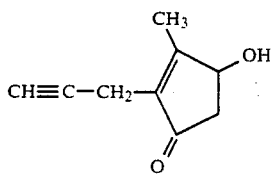

with vinyl halide in the presence of a palladium catalyst, a copper catalyst and a tertiary amine to obtain a cyclopentenolone derivative of the formula (I)

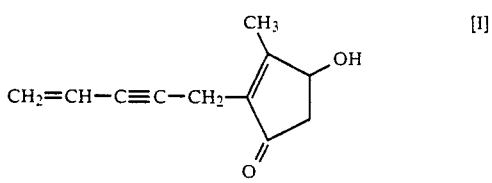

and reacting the cyclopentenolone derivative with zinc an the aqueous alcohol solvent.

3. The process of claim 2, wherein the palladium catalyst is a palladium phosphine complex.

4. The process of claim 2, wherein the copper catalyst is cuprous halide.

5. The process of claim 2, wherein the tertiary amine is a tertiary amine having three lower alkyl groups.

6. The process of claim 1, wherein the step includes the steps of selecting the amount used of the vinyl halide within the range of from 1 to 20 equivalents, the amount used of the palladium catalyst within the range of from 0.001 to 0.5 equivalent, the amount used of the copper catalyst within the range of from 0.001 to 0.5 equivalent and the amount used of the tertiary amine within the range of from 1 to 10 equivalents, all per equivalent of the propargylcyclopentenolone and carrying out the reaction at a temperature within the range of from 5° to 50° C.

7. The process of claim 1, wherein the palladium catalyst is a palladium phosphine complex.

8. The process of claim 1, wherein the copper catalyst is cuprous halide.

9. The process of claim 1, wherein the tertiary amine is a tertiary amine having three lower alkyl groups.

* * * * *